(12) United States Patent
Herbst et al.

(10) Patent No.: US 7,947,297 B2
(45) Date of Patent: *May 24, 2011

(54) MIXTURES OF PHENOLIC AND INORGANIC MATERIALS WITH ANTIMICROBIAL ACTIVITY

(75) Inventors: Heinz Herbst, Loerrach (DE); Urs Stadler, Madison, NJ (US)

(73) Assignee: BASF SE, Ludwigshafen (DE)

( * ) Notice: Subject to any disclaimer, the term of this patent is extended or adjusted under 35 U.S.C. 154(b) by 775 days.

This patent is subject to a terminal disclaimer.

(21) Appl. No.: 10/992,526

(22) Filed: Nov. 18, 2004

(65) Prior Publication Data

US 2005/0131100 A1  Jun. 16, 2005

Related U.S. Application Data

(63) Continuation of application No. 10/323,239, filed on Dec. 18, 2002, which is a continuation of application No. 09/957,959, filed on Sep. 21, 2001, now Pat. No. 6,585,989.

(60) Provisional application No. 60/234,433, filed on Sep. 21, 2000.

(51) Int. Cl.
*A01N 25/34* (2006.01)
*A61K 33/38* (2006.01)
*A61K 31/05* (2006.01)
*A61K 31/075* (2006.01)

(52) U.S. Cl. ......... 424/404; 424/618; 514/737; 514/721

(58) Field of Classification Search ............. 523/122; 424/405, 404, 600, 618, 617, 630, 645, 684; 514/737, 721
See application file for complete search history.

(56) References Cited

U.S. PATENT DOCUMENTS

| | | | | |
|---|---|---|---|---|
| 4,775,585 A * | 10/1988 | Hagiwara et al. | ............. | 428/323 |
| 4,824,661 A | 4/1989 | Wagner | ............. | 424/52 |
| 4,911,898 A | 3/1990 | Hagiwara et al. | ............. | 423/118 |
| 4,911,899 A | 3/1990 | Hagiwara et al. | ............. | 423/118 |
| 5,357,636 A | 10/1994 | Dresdner, Jr. et al. | ............. | 2/161.7 |
| 5,455,024 A | 10/1995 | Winston et al. | ............. | 424/52 |
| 5,723,110 A * | 3/1998 | Yamamoto et al. | ............. | 424/401 |
| 5,789,470 A | 8/1998 | Herbst et al. | ............. | 524/100 |
| 6,071,542 A * | 6/2000 | Tanimoto et al. | ............. | 424/618 |
| 6,129,782 A | 10/2000 | Brodie et al. | ............. | 106/15.05 |
| 6,217,889 B1 * | 4/2001 | Lorenzi et al. | ............. | 424/401 |
| 6,240,879 B1 * | 6/2001 | Denesuk et al. | ............. | 119/709 |
| 6,585,989 B2 | 7/2003 | Herbst et al. | ............. | 424/404 |

FOREIGN PATENT DOCUMENTS

| | | |
|---|---|---|
| JP | 03153745 | 7/1991 |
| WO | 96/22114 | 7/1996 |
| WO | 00/52088 | 9/2000 |
| WO | 00/57933 | 10/2000 |

OTHER PUBLICATIONS

Ullmann's Encyclopedia of Industrial Chemistry Fifth, Completely Revised Edition vol. A28, p. 475, 1996.
Kirk-Othmer Encyclopedia of Chemical Technology Fifth Edition, vol. 16, pp. 811-813, 2004.

* cited by examiner

*Primary Examiner* — Blessing M Fubara
(74) *Attorney, Agent, or Firm* — Tyler A. Stevenson

(57) ABSTRACT

Plastic films, fibers and articles are provided long-term antimicrobial activity with a combination of certain phenolic and inorganic antimicrobial agents. The plastic films, fibers and articles with antimicrobial activity exhibit superior resistance to discoloration, may be processed at high temperature, and maintain physical properties upon weathering, especially upon exposure to ultraviolet radiation.

8 Claims, No Drawings

MIXTURES OF PHENOLIC AND INORGANIC MATERIALS WITH ANTIMICROBIAL ACTIVITY

This application is a continuation of application Ser. No. 10/323,239, filed Dec. 18, 2002, pending, which is a continuation of application Ser. No. 09/957,959, filed Sep. 21, 2001, now U.S. Pat. No. 6,585,989, which claims the benefit under 35 U.S.C. 119(e) of U.S. Provisional Application No. 60/234,433, filed Sep. 21, 2000.

The present invention relates to combinations of phenolic and inorganic compounds which exhibit excellent antimicrobial activity when incorporated into a substrate resin, which mixtures do not exhibit the negative effects associated with the use of either alone. Plastic articles manufactured via a variety of processes from such resins are provided long term antimicrobial activity and exhibit superior resistance to discoloration and maintenance of physical properties, especially upon exposure to ultraviolet radiation.

Triclosan, or Irgaguard®, Ciba Specialty Chemicals, 2,4,4'-trichloro-2'-hydroxydiphenyl ether, is a known antimicrobial for plastics applications. It is known to have high activity against numerous gram-positive and gram-negative bacterial. It can be incorporated as a neat material or via a masterbatch into a variety of polymer substrates, for example, polyethylenes such as LDPE, HDPE, MDPE, polypropylene (PP), acrylonitrile-butadiene-styrene terpolymer (ABS), styrene-acrylonitrile copolymer (SAN), polystyrene (PS), polyacrylates, polymethyl methacrylate (PMMA), polyamide, polyesters, polyvinyl chloride (PVC), polymer latex, polyurethane (PUR), thermoplastic polyurethane (TPU), unsaturated polyester (UP), urea formaldehyde resin (UF), etc. Irgaguard® exhibits high activity at the surface of plastic articles and the activity remains after repeated washing of plastic articles. Further, Irgaguard® has a good toxicological profile.

Disadvantages of Irgaguard® are that plastic articles formulated with it exhibit strong discoloration upon weathering. For example, polypropylene samples containing lrgaguard® exposed in a Xenon Arc Weather-Ometer at 035 W/m$^2$, 63° C. discolor within hours. Further, processing at temperatures greater than 250° C. is poblematic due to the volatility of Irgaguard®.

Silver based materials, such as colloidal silver, silver nitrate, silver sulfate, silver chloride, silver complexes and silver ion containing zeolites are known antimicrobial agents for plastic articles. Silver compounds exhibit high activity against microorganisms and they have a good toxicological profile. High processing temperatures are possible with silver compounds (greater than 300° C.).

Disadvantages of silver based antimicrobials are that plastic articles containing them often exhibit discloloration upon weathering, and the activity on the surface of the articles is often lost after repeated washing.

It has been found, surprisingly, that a combination of certain phenolic compounds with certain inorganic compounds avoids the disadvantages of using either lrgaguard® or silver based antimicrobials alone in plastic articles while providing excellent long-term antimicrobial activity to the articles.

OBJECTS OF THE INVENTION

An object of the present invention is to provide a novel mixture of antimicrobial agents for plastics applications.

Another object of the invention is to provide plastic articles or films with antimicrobial activity which also exhibit superior resistance to discoloration, may be processed at high temperatures, and which maintain physical properties upon weathering, especially upon exposure to UV radiation.

DETAILED DESCRIPTION

The instant invention pertains to a novel mixture of antimicrobial agents for plastics applications which comprises
  a) at least one phenolic antimicrobial compound, and
  b) at least one inorganic antimicrobial compound,
wherein
the phenolic antimicrobial compound is of the formula (I)

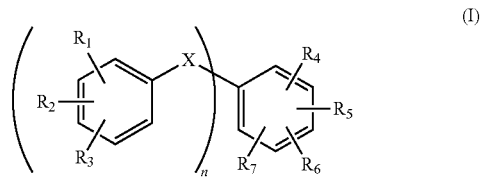

wherein
n is 0 or 1,
$R_1$ and $R_2$ are hydrogen or chlorine,
$R_3$ is hydrogen or hydroxyl,
$R_4$, $R_5$ and $R_6$ are hydrogen or chlorine,
$R_7$ is hydroxyl, and
X is —O— or —CH$_2$—,
and wherein the inorganic antimicrobial compound is selected from the group consisting of zinc oxide, copper and copper compounds, colloidal silver, silver nitrate, silver sulphate, silver chloride, silver complexes, metal-containing zeolites and surface-modified metal-containing zeolites,
and wherein the ratio of components a):b) is from about 1:9 to about 9:1.

Preferred phenolic antimicrobial compounds of component a) are o-benzyl-phenol, 2-benzyl-4-chloro-phenol, 2,4,4'-trichloro-2'-hydroxydiphenyl ether, 4,4'-dichloro-2-hydroxydiphenyl ether, 5-chloro-2-hydroxy-diphenyl-methane, mono-chloro-o-benzyl-phenol, 2,2'-methylenbis-(4-chlorophenol) and 2,4,6-trichlorophenol.

Most preferred phenolic antimicrobial compounds of component a) are 2,4,4'-trichloro-2'-hydroxydiphenyl ether and 4,4'-dichloro-2-hydroxydiphenyl ether.

The metal-containing zeolites of component b) are those such as described in U.S. Pat. Nos. 4,775,585, 4,911,898, 4,911,899 and 6,071,542, the disclosures of which are hereby incorporated by reference. A zeolite is generally aluminosilicate having a three dimensionally grown skeleton structure and is generally represented by $xM_{2/n}O.Al_2O_3.ySiO_2.zH_2O$, written with $Al_2O_3$ as a basis, wherein M represents an ion-exchangeable metal ion, which is usually the ion of a monovalent or divalent metal; n corresponds to the valence of the metal; x is a coefficient of the metal oxide; y is a coefficient of silica; and z is the number of water of crystallization. The zeolites of the present invention have a specific surface area of at least 150 m$^2$/g.

Antibacterial metals for use in metal-containing zeolites include silver, copper, zinc, mercury, tin, lead, bismuth, cadmium, chromium, cobalt, nickel, zirconium, or a combination of two or more of these metals. Preference is given to silver, copper, zinc and zirconium, or a combination of these. Especially preferred metals are silver alone or a combination of silver with copper, zinc or zirconium.

Particularly preferred inorganic antimicrobial compounds of component b) are surface-modified metal-containing zeolites according to U.S. Pat. No. 6,071,542.

Especially preferred is the antimicrobial mixture wherein component a) is 2,4,4'-trichloro-2'-hydroxydiphenyl ether and wherein the inorganic antimicrobial compound of component b) is a surface-modified silver-containing zeolite. The term "silver-containing" includes the combination of silver with other metals such as zinc, copper and zirconium. BACTEKILLER BM-102GA (Kanebo) is an example of a surface-modified silver-containing zeolite according to U.S. Pat. No. 6,071,542.

In addition to zeolites, it is also contemplated that antibacterial metals such as silver, silver compounds and silver complexes may be supported on other inert materials, for example $SiO_2$, $TiO_2$ and glass.

The instant invention also pertains to plastic films, fibers or articles that comprise the novel mixture of components a) and b).

The novel antimicrobial mixture of components a) and b) may be incorporated into the plastic resin prior to its being subjected to such manufacturing processes as blown film, rotational molding, fiber spinning, etc. The mixture of components a) and b) is able to withstand demanding processing conditions such as high temperature, e.g. temperatures greater than 200° C.

The plastic films, fibers and articles comprising the present antimicrobial mixture of components a) and b) is suitable for outdoor exposure; they are resistant to weathering and UV light degradation.

The antimicrobial mixture of components a) and b) exhibit good long-term activity and a good toxicological profile.

Triclosan containing plastic samples lead to a strong discoloration within a very short time when exposed to weathering. Plastic samples containing the present combination of components a) and b) exhibit only minimal color changes.

Triclosan containing plastic samples exhibit a reduced light stability. Plastic samples containing the present combination of components a) and b) exhibit physical properties that are comparable to a control formulation without antimicrobial agents.

The plastic films, fibers and articles of the present invention are advantageously employed for applications that require long-term hygienic activity on the surface, e.g., medical devices, hand rails, door handles, etc. The antimicrobial plastic films, fibers and articles of the present invention are used for example in hospitals, households, public institutions, ventilation systems, air cleaning and air conditioning systems and waste disposal systems. Plastic articles exposed to outdoor weathering that may have incorporated therein the antimicrobial mixture of the present invention are for example waste containers, swimming pool equipment, outdoor swing set equipment, slides and the like, and stadium seats.

The plastic films, fibers and articles of the present invention exhibit high antimicrobial activity at the surface. The antimicrobial activity remains after repeated washings.

The plastic films, fibers and articles of the present invention, that is to say, the plastic materials, may also have incorporated therein one or more of the following known additives:

1. Antioxidants
   1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.
   1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
   1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.
   1.4. Tocopherols, for example α-tocopherol, β-tocopherol, γ-tocopherol, δ-tocopherol and mixtures thereof (Vitamin E).
   1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.
   1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methylphenyl)dicyclopentadiene, bis[2-(3'tert-butyl-2-hydroxy-5-methylbenzyl)-6-tert-butyl-4-methylphenyl] terephthalate, 1,1-bis-(3,5-dimethyl-2-hydroxyphenyl) butane, 2,2-bis-(3,5-di-tert-butyl-4-hydroxyphenyl) propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.
   1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl) sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl) isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxy-benzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris (3,5-di-tert-butyl-4-hydroxy-phenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)ox-amide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl) diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl) amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl) amino]ethane, 1,2-bis(phenylamino)propane, (o-tolyl) biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004, 896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3, 5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy) carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole,2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4, 4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS #7443-25-6), and Sanduvor® PR31, di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2, 6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6, 6-tetramethylpiperidyl)sebacate, bis(1-octyloxy-2,2,6, 6-tetramethyl-piperidyl)succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl )-1,3, 5-triazine and 1,2-bis(3-amino-propylamino)ethane, the condensate of 2-chloro-4,6-di-(4-n-butylamino-1,2,2,6, 6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in GB-A-2301106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2301106.

The sterically hindered amine may also be one of the compounds described in EP 782994, for example compounds as described in claims 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl)succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxy-ethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)-phenyl]-s-triazine, 2,4-bis(2,4-dimethylphenyl)-6-[2-hydroxy-4-(3-benzyloxy-2-hydroxy-propyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)-phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:

Tris(2,4-di-tert-butylphenyl)phosphite (Irgafos® 9168, Ciba Specialty Chemicals Corp.), tris(nonylphenyl)phosphite,

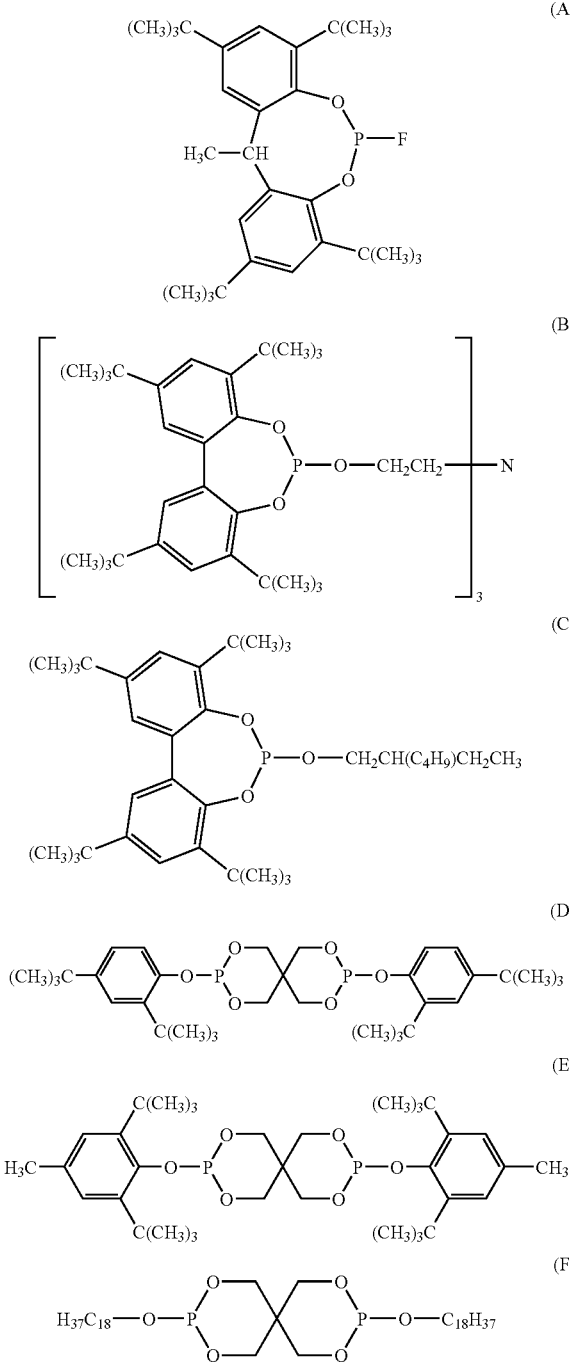

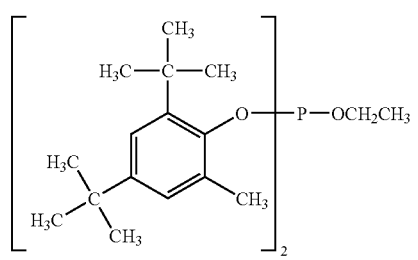

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), Cyasorb® 3638 (CAS #18600-59-4), and blowing agents.

16. Other biocides, for example fungicides such as 3,5-dimethyl-tetrahydro-1,3,5-2H-thiodiazin-2-thione, Bis-tributyltinoxide, 4.5-dichlor-2-n-octyl-4-isothiazolin-3-one, N-butyl-benzisothiazoline, 10.10'-oxybisphenoxyarsine, zinc-2-pyridinthiol-1-oxide, etc., and algicides such as 2-methylthio-4-cyclopropylamino-6-($\alpha,\beta$-dimethylpropylamino)-s-triazine, 2-methylthio-4-cyclopropylamino-6-tert-butylamino-s-triazine, 2-methylthio-4-ethylamino-6-($\alpha,\beta$-dimethylpropylamino)-s-triazine, etc.

In general the plastic resins with antimicrobial activity according to the present invention may be selected from:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE) and medium density polyethylene (MDPE).

Polyolefins, i.e. the polymers of monoolefins exemplified in the preceding paragraph, preferably polyethylene and polypropylene, can be prepared by different, and especially by the following, methods:

a) radical polymerization (normally under high pressure and at elevated temperature).

b) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EM and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/unsaturated ester, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, SAN, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bis-glycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4, -trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides and polybenzimidazoles.
18. Polyesters derived from dicarboxylic acids and diols and/or from hydroxycarboxylic acids or the corresponding lactones, for example polyethylene terephthalate, polytrimethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS. Polyesters and polyester copolymers as defined in U.S. Pat. No. 5,807,932 (column 2, line 53 ), incorporated herein by reference.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, polyisocyanates or epoxy resins.
26. Crosslinked epoxy resins derived from polyepoxides, for example from bis glycidyl ethers or from cycloaliphatic diepoxides.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/-EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

Preferably, the plastic resin is selected from the group consisting of LDPE, HDPE, MDPE, PP, ABS, SAN, PS, PMMA, PET, polyamide, PVC, polymer latex, PUR, TPU, UF and UP.

The mixture of components a) and b) is preferably present in the antimicrobial plastic film, fiber or article in an amount of about 0.005 to about 10% by weight, relative to the plastic material. An amount of from about 0.01 to about 5% by weight or about 0.05 to about 3% by weight of the mixture of components a) and b) relative to the plastic material is especially preferred.

The mixture of components a) and b) and optional further additives may be added to the plastic resin, e.g. the polyolefin, individually or mixed with one another. If desired, the individual components of an additive mixture can be mixed with one another in the melt (melt blending) before incorporation into the plastic material.

The incorporation of the mixture of components a) and b) and optional further additives into the plastic material is carried out by known methods such as dry mixing in the form of a powder, or wet mixing in the form of solutions or suspensions. Components a) and b) and optional further additives may be incorporated, for example, before or after molding or also by applying the dissolved or dispersed stabilizer mixture to the plastic material, with or without subsequent evaporation of the solvent. The mixture of components a) and b) and optional further additives can also be added to the plastic material in the form of a masterbatch which contains these components in a concentration of, for example, about 2.5% to about 70% by weight; in such operations, the polymer can be used in the form of powder, granules, solutions, suspensions or in the form of latices.

If added to a plastic resin in the form of a masterbatch or concentrate, the novel antimicrobial mixture of components a) and b) is added via carriers such as LDPE, HDPE, MDPE, PP, ABS, SAN, PS, acrylates, PMMA, polyamide, polyesters, PVC, polymer latex, styrene, polyol, TPU, unsaturated esters, urea, paraformaldehyde, water emulsion, etc. The total concentration of a)+b) in the carriers is from about 2.5% to about 70% by weight based on the weight of the carrier.

Components a) and b) and optional further additives can also be added before, during or after polymerization or crosslinking.

Components a) and b) and optional further additives can be incorporated into the plastic material in pure form or encapsulated in waxes, oils or polymers.

Components a) and b) and optional further additives can also be sprayed onto the plastic material. They are able to dilute other additives (for example the conventional additives indicated above) or monomers or their melts so that they can be sprayed also together with these additives onto the plastic material. Addition by spraying during the deactivation of the polymerization catalysts is particularly advantageous, it being possible to carry out spraying using, for example, the steam used for deactivation.

In the case of spherically polymerized polyolefins it may, for example, be advantageous to apply components a) and b) and optionally together with other additives, by spraying.

The following examples illustrate the invention in more detail. They are not to be construed as limiting the instant invention in any manner whatsoever. The invention is declared to cover all changes and modifications of the specific examples which do not constitute departure from the spirit and scope of the invention. Parts and percentages are by weight.

EXAMPLE 1

High density polyethylene, Borealis MS 6591, is dry blended with the antimicrobial agents set forth in Table 1. The levels are percent by weight based on the HDPE. The mixtures are compounded with a twin screw at a maximum temperature of 220° C. The samples are injection molded into 2 mm plaques at a maximum temperature of 220° C. The plaques are subjected to accelerated weathering in a Ci65 Xenon Arc Weather-Ometer at 63° C., 0.35 W/m$^2$ with a spray cycle. Yellowness Index results are found in Table 1.

TABLE 1

| Antimicrobial Agents | 0 h | 24 h | 48 h | 96 h | 500 h |
|---|---|---|---|---|---|
| none | 1.9 | 2.7 | 1.9 | 0.3 | −0.8 |
| 0.2% Irgaguard ® B1000 | 4.0 | 57.1 | 60.8 | 62.5 | 66.9 |
| 0.2% Irgaguard ® B1000 + 0.1% BM-102GA | 1.1 | 38.9 | 42.5 | 45.4 | 49.9 |
| 0.5% Irgaguard ® B1000 + 0.1% BM-102GA | 2.2 | 21.2 | 27.9 | 33.1 | 33.4 |

Irgaguard ® B1000 is 2,4,4'-trichloro-2'-hydroxydiphenyl ether, Ciba Specialty Chemicals. BM-102GA (Kanebo) is a surface-modified silver-containing zeolite.

It can be seen that the formulations of the present invention, using a combination of antimicrobial agents of components a) and b), provide superior resistance to yellowing upon accelerated weathering.

EXAMPLE 2

Polypropylene homopolymer, Montell Pro-fax 6301, is dry blended with the antimicrobial agents set forth in Table 2. The levels are percent by weight based on the polypropylene. The mixtures are additionally formulated with 0.06% Irgastab® FS-301, 0.06% Tinuvin® 783 and 0.05% calcium stearate. The polypropylene samples are spun into fibers at 260° C. The fibers are subjected to accelerated weathering in a Ci65 Xenon Arc Weather-Ometer at 63° C., 0.35 W/m$^2$ with a spray cycle. Yellowness Index results are found in Table 2.

TABLE 2

| Antimicrobial Agents | 0 h | 12 h | 68 h | 157 h | 392 h |
|---|---|---|---|---|---|
| none | 1.7 | 1.8 | 1.5 | 1.1 | 1.4 |
| 0.5% Irgaguard ® B1000 | 2.0 | 24.1 | 16.9 | 9.5 | failure |
| 0.25% Irgaguard ® B1000 + 0.25% BM-102GA | 1.9 | 9.3 | 7.3 | 4.9 | 2.8 |

It can be seen that the formulations of the present invention, using a combination of antimicrobial agents of components a) and b), provide superior resistance to yellowing upon accelerated weathering.

Irgaguard® B1000 is 2,4,4'-trichloro-2'-hydroxydiphenyl ether, Ciba Specialty Chemicals. BM-102GA (Kanebo) is a surface-modified silver-containing zeolite.

Tinuvin® 783 is a combination of sterically hindered amine light stabilizers available from Ciba Specialty Chemicals, Tinuvin® 622 and Chimassorb® 944:

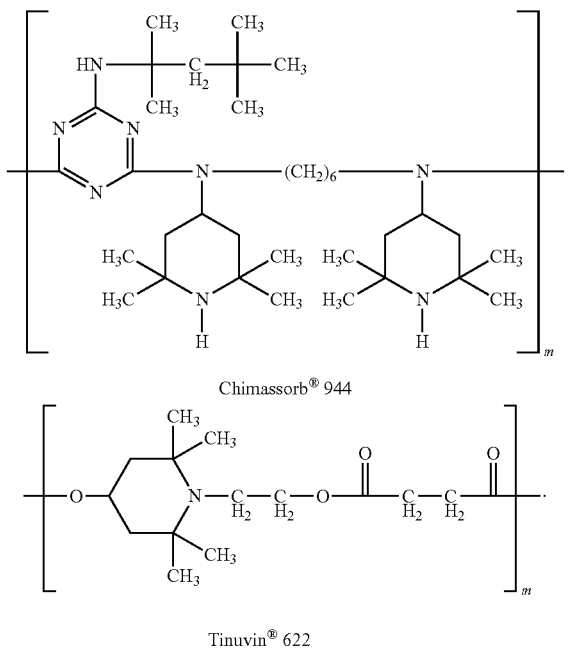

Chimassorb® 944

Tinuvin® 622

Irgastab® FS-301, Ciba Specialty Chemicals, is a combination of Irgafos® 168 and Irgastab® FS-042. Irgafos® 168 is tris-(2,4-di-tert-butylphenyl)phosphite. Irgastab® FS-042 is the N,N-di(alkyl)hydroxylamine produced by the direct oxidation of N,N-di(hydrogenated tallow)amine.

What is claimed is:

1. A plastic composition which comprises
a plastic resin selected from polyamide and acrylonitrile-butadiene-styrene terpolymer and incorporated therein,
a mixture of antimicrobial agents which comprises
a) 2,4,4'-trichloro-2'-hydroxydiphenyl ether and
b) an antibacterial silver-supporting zeolite,
wherein the weight ratio of components a):b) is from 2:1 to 1:1 and
wherein the mixture of a) and b) is present from about 0.05 to about 3% by weight, based on the weight of the polyamide or acrylonitrile-butadiene-styrene terpolymer.

2. A composition according to claim 1 which additionally comprises at least one co-additive selected from the group consisting of antioxidants, ultraviolet light absorbers, hindered amines, phosphites or phosphonites, hydroxylamines, nitrones, benzofuran-2-ones, thiosynergists, polyamide stabilizers, metal stearates, nucleating agents, fillers, reinforcing agents, lubricants, emulsifiers, dyes, pigments, optical brighteners, flame retardants, antistatic agents and blowing agents.

3. A composition according to claim 1 which additionally comprises at least one co-additive selected from the group consisting of the hindered amines.

4. A composition according to claim 1 wherein component b) is a surface-modified antibacterial silver-supporting zeolite.

5. A composition according to claim 1 wherein the weight ratio of components a):b) is 1:1.

6. A composition according to claim 1 wherein the weight ratio of components a):b) is 2:1.

7. A composition according to claim 4 wherein the weight ratio of components a):b) is 1:1.

8. A composition according to claim 4 wherein the weight ratio of components a):b) is 2:1.

* * * * *